(12) United States Patent
Krimsky et al.

(10) Patent No.: US 11,219,489 B2
(45) Date of Patent: Jan. 11, 2022

(54) DEVICES AND SYSTEMS FOR PROVIDING SENSORS IN PARALLEL WITH MEDICAL TOOLS

(71) Applicant: COVIDIEN LP, Mansfield, MA (US)

(72) Inventors: William S. Krimsky, Forest Hill, MD (US); Joshua B. Stopek, Minneapolis, MN (US)

(73) Assignee: COVIDIEN LP, Mansfield, MA (US)

( * ) Notice: Subject to any disclaimer, the term of this patent is extended or adjusted under 35 U.S.C. 154(b) by 579 days.

(21) Appl. No.: 16/150,340

(22) Filed: Oct. 3, 2018

(65) Prior Publication Data

US 2019/0125453 A1 May 2, 2019

Related U.S. Application Data

(60) Provisional application No. 62/579,295, filed on Oct. 31, 2017.

(51) Int. Cl.
| | | |
|---|---|---|
| *A61B 34/20* | (2016.01) | |
| *A61B 1/267* | (2006.01) | |
| *A61B 1/00* | (2006.01) | |
| *A61B 8/00* | (2006.01) | |

(Continued)

(52) U.S. Cl.
CPC .......... *A61B 34/20* (2016.02); *A61B 1/00114* (2013.01); *A61B 1/00135* (2013.01); *A61B 1/2676* (2013.01); *A61B 8/42* (2013.01); *A61B 1/018* (2013.01); *A61B 17/00234* (2013.01); *A61B 2017/00336* (2013.01); *A61B 2017/00477* (2013.01); *A61B 2034/2051* (2016.02);

(Continued)

(58) Field of Classification Search
CPC .................. A61B 1/00135; A61B 8/42; A61B 2017/003336; A61B 34/20
See application file for complete search history.

(56) References Cited

U.S. PATENT DOCUMENTS

| | | | |
|---|---|---|---|
| 1,576,781 | A | 3/1926 | Phillips |
| 1,735,726 | A | 11/1929 | Bornhardt |
| 2,407,845 | A | 9/1946 | Nemeyer |

(Continued)

FOREIGN PATENT DOCUMENTS

| | | |
|---|---|---|
| CA | 964149 | 3/1975 |
| DE | 3042343 A1 | 6/1982 |

(Continued)

OTHER PUBLICATIONS

Extended European Search Report issued in corresponding Application No. EP 18203515.4 dated Apr. 11, 2019 (9 pages).

(Continued)

*Primary Examiner* — Joanne M Hoffman
*Assistant Examiner* — Sean V Blinder
(74) *Attorney, Agent, or Firm* — Carter, DeLuca & Farrell LLP

(57) ABSTRACT

Disclosed are systems, devices, and methods for using sensor sleeves with surgical tools. In an aspect of the present disclosure, a sensor sleeve includes a tubular body defining a central longitudinal axis and having a lumen defined therethrough, the tubular body being configured to receive a tool, a plurality sensors attached to the tubular body, a cabling extending distally from the tubular body, and an interface connector coupled to the cabling and configured to interface with a navigation system.

16 Claims, 9 Drawing Sheets

(51) Int. Cl.
*A61B 17/00* (2006.01)
*A61B 1/018* (2006.01)
(52) U.S. Cl.
CPC ............... *A61B 2034/2055* (2016.02); *A61B 2034/2063* (2016.02)

(56) References Cited

U.S. PATENT DOCUMENTS

| | | |
|---|---|---|
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,447,224 A | 5/1984 | DeCant, Jr. et al. |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,769,005 A | 9/1988 | Ginsburg et al. |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |

(56) References Cited

U.S. PATENT DOCUMENTS

| | | |
|---|---|---|
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aamio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beally et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,403,321 A | 4/1995 | DiMarco |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |

(56) References Cited

U.S. PATENT DOCUMENTS

| | | |
|---|---|---|
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,522,815 A | 6/1996 | Durgin, Jr. et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,935,160 A | 8/1999 | Auricchio et al. |
| 5,938,603 A | 8/1999 | Ponzi |
| 5,938,694 A | 8/1999 | Jaraczewski et al. |
| 5,947,980 A | 9/1999 | Jensen et al. |

(56) References Cited

U.S. PATENT DOCUMENTS

| | | |
|---|---|---|
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,964,793 A | 10/1999 | Rutten et al. |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,112,111 A | 8/2000 | Glantz |
| 6,118,845 A | 9/2000 | Simon et al. |
| 6,122,538 A | 9/2000 | Sliwa, Jr. et al. |
| 6,122,541 A | 9/2000 | Cosman et al. |
| 6,129,698 A | 10/2000 | Beck |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,201,387 B1 | 3/2001 | Govari |
| 6,203,493 B1 | 3/2001 | Ben-Haim |
| 6,203,497 B1 | 3/2001 | Dekel et al. |
| 6,210,362 B1 | 4/2001 | Ponzi |
| 6,211,666 B1 | 4/2001 | Acker |
| 6,213,995 B1 | 4/2001 | Steen et al. |
| 6,216,026 B1 | 4/2001 | Kuhn et al. |
| 6,216,027 B1 | 4/2001 | Willis et al. |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,246,231 B1 | 6/2001 | Ashe |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,304,769 B1 | 10/2001 | Arenson et al. |
| 6,314,310 B1 | 11/2001 | Ben-Haim et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,351,659 B1 | 2/2002 | Vilsmeier |
| 6,366,799 B1 | 4/2002 | Acker et al. |
| 6,373,240 B1 | 4/2002 | Govari |
| 6,381,485 B1 | 4/2002 | Hunter et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,534,982 B1 | 3/2003 | Jakab |
| 6,551,325 B2 | 4/2003 | Neubauer et al. |
| 6,580,938 B1 | 6/2003 | Acker |
| 6,584,174 B2 | 6/2003 | Schubert et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,618,612 B1 | 9/2003 | Acker et al. |
| 6,628,980 B2 | 9/2003 | Atalar et al. |
| 6,640,128 B2 | 10/2003 | Vilsmeier et al. |
| 6,650,927 B1 | 11/2003 | Keidar |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,711,429 B1 | 3/2004 | Gilboa et al. |
| 6,788,967 B2 | 9/2004 | Ben-Haim et al. |
| 6,834,201 B2 | 12/2004 | Gillies et al. |
| 6,995,729 B2 | 2/2006 | Govari et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,248,914 B2 | 7/2007 | Hastings et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,497,029 B2 | 3/2009 | Plassky et al. |
| 7,505,809 B2 | 3/2009 | Strommer et al. |
| 7,536,218 B2 | 5/2009 | Govari et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |

(56) References Cited

U.S. PATENT DOCUMENTS

| | | |
|---|---|---|
| 7,652,468 B2 | 1/2010 | Kruger et al. |
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,972 B2 | 4/2010 | Verard et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,720,521 B2 | 5/2010 | Chang et al. |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 7,809,421 B1 | 10/2010 | Govari |
| 8,206,380 B2 | 6/2012 | Lenihan et al. |
| 8,611,984 B2 | 12/2013 | Greenburg et al. |
| 8,731,684 B2 | 5/2014 | Carr et al. |
| 8,926,605 B2 | 1/2015 | McCarthy et al. |
| 8,954,161 B2 | 2/2015 | McCarthy et al. |
| 8,961,506 B2 | 2/2015 | McCarthy et al. |
| 9,113,813 B2 | 8/2015 | Greenburg et al. |
| 9,121,774 B2 | 9/2015 | Brannan |
| 2001/0007918 A1 | 7/2001 | Vilsmeier et al. |
| 2001/0031919 A1 | 10/2001 | Strommer et al. |
| 2001/0034530 A1 | 10/2001 | Malackowski et al. |
| 2001/0036245 A1 | 11/2001 | Kienzle et al. |
| 2002/0062203 A1 | 5/2002 | Gilboa |
| 2002/0095081 A1 | 7/2002 | Vilsmeier |
| 2002/0128565 A1 | 9/2002 | Rudy |
| 2002/0173689 A1 | 11/2002 | Kaplan |
| 2002/0193686 A1 | 12/2002 | Gilboa |
| 2003/0018251 A1 | 1/2003 | Solomon |
| 2003/0074011 A1 | 4/2003 | Gilboa et al. |
| 2003/0086599 A1 | 5/2003 | Armato et al. |
| 2003/0142753 A1 | 7/2003 | Gunday |
| 2003/0160721 A1 | 8/2003 | Gilboa et al. |
| 2004/0015049 A1 | 1/2004 | Zaar |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0138548 A1 | 7/2004 | Strommer et al. |
| 2004/0169509 A1 | 9/2004 | Czipott et al. |
| 2004/0249267 A1 | 12/2004 | Gilboa |
| 2005/0033149 A1 | 2/2005 | Strommer et al. |
| 2005/0085715 A1 | 4/2005 | Dukesherer et al. |
| 2005/0107688 A1 | 5/2005 | Strommer |
| 2005/0119527 A1 | 6/2005 | Banik et al. |
| 2005/0197566 A1 | 9/2005 | Strommer et al. |
| 2006/0015126 A1 | 1/2006 | Sher |
| 2006/0058647 A1 | 3/2006 | Strommer et al. |
| 2006/0064006 A1 | 3/2006 | Strommer et al. |
| 2006/0149134 A1 | 7/2006 | Soper et al. |
| 2007/0135803 A1 | 6/2007 | Belson |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0265639 A1 | 11/2007 | Danek et al. |
| 2007/0287901 A1 | 12/2007 | Strommer et al. |
| 2008/0086051 A1 | 4/2008 | Voegele |
| 2008/0097187 A1 | 4/2008 | Gielen et al. |
| 2008/0118135 A1 | 5/2008 | Averbuch et al. |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2009/0182224 A1 | 7/2009 | Shmarak et al. |
| 2012/0035603 A1 | 2/2012 | Lenihan |
| 2012/0289776 A1 | 11/2012 | Keast et al. |
| 2013/0274720 A1* | 10/2013 | Brannon ............ A61B 17/3421 606/1 |
| 2014/0051987 A1 | 2/2014 | Kowshik et al. |
| 2015/0073217 A1* | 3/2015 | Powell ............... A61B 1/00082 600/116 |
| 2015/0105765 A1 | 4/2015 | Panescu et al. |
| 2016/0000303 A1 | 1/2016 | Klein et al. |
| 2016/0000517 A1 | 1/2016 | Kehat et al. |
| 2016/0051221 A1 | 2/2016 | Dickhans et al. |
| 2016/0296105 A1* | 10/2016 | Ramsey ............. A61B 1/00103 |
| 2017/0077642 A1* | 3/2017 | Benham ............. H01R 13/5202 |

FOREIGN PATENT DOCUMENTS

| | | |
|---|---|---|
| DE | 3508730 A1 | 9/1986 |
| DE | 3520782 A1 | 12/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T1 | 11/2002 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0419729 A1 | 4/1991 |
| EP | 0427358 A1 | 5/1991 |
| EP | 0456103 A2 | 11/1991 |
| EP | 0581704 A1 | 2/1994 |
| EP | 0651968 A1 | 5/1995 |
| EP | 0655138 B1 | 5/1995 |
| EP | 0894473 A2 | 2/1999 |
| EP | 0908146 A2 | 4/1999 |
| EP | 0930046 A2 | 7/1999 |
| EP | 1078644 A1 | 2/2001 |
| EP | 1374793 A1 | 1/2004 |
| EP | 2096523 A1 | 9/2009 |
| EP | 2123216 A1 | 11/2009 |
| EP | 2238901 A2 | 10/2010 |
| EP | 2364660 A1 | 9/2011 |
| EP | 2377457 A1 | 10/2011 |
| FR | 2417970 A1 | 9/1979 |
| FR | 2541498 A1 | 8/1984 |
| FR | 2541498 A1 * | 8/1984 ........... H01B 7/0815 |
| FR | 2618211 A1 | 1/1989 |
| GB | 2094590 A | 9/1982 |
| GB | 2164856 A | 4/1986 |
| JP | 63240851 A | 10/1988 |
| JP | 03267054 A | 11/1991 |
| JP | 06194639 A | 7/1994 |
| WO | 8809151 A1 | 12/1988 |
| WO | 8905123 A1 | 6/1989 |
| WO | 9005494 A1 | 5/1990 |
| WO | 9103982 A1 | 4/1991 |
| WO | 9104711 A1 | 4/1991 |
| WO | 9107726 A1 | 5/1991 |
| WO | 9203090 A1 | 3/1992 |
| WO | 9206645 A1 | 4/1992 |
| WO | 9404938 A1 | 3/1994 |

(56) References Cited

FOREIGN PATENT DOCUMENTS

| | | | |
|---|---|---|---|
| WO | 9423647 | A1 | 10/1994 |
| WO | 9424933 | A1 | 11/1994 |
| WO | 9507055 | A1 | 3/1995 |
| WO | 9605768 | A1 | 2/1996 |
| WO | 9611624 | A2 | 4/1996 |
| WO | 9632059 | A1 | 10/1996 |
| WO | 9700043 | A1 | 1/1997 |
| WO | 97/29684 | A1 | 8/1997 |
| WO | 9736192 | A1 | 10/1997 |
| WO | 9749453 | A1 | 12/1997 |
| WO | 9808554 | A1 | 3/1998 |
| WO | 9838908 | A1 | 9/1998 |
| WO | 9915097 | A2 | 4/1999 |
| WO | 9918852 | A1 | 4/1999 |
| WO | 9921498 | A1 | 5/1999 |
| WO | 9923956 | A1 | 5/1999 |
| WO | 9926549 | A1 | 6/1999 |
| WO | 9927839 | A2 | 6/1999 |
| WO | 9929253 | A1 | 6/1999 |
| WO | 9933406 | A1 | 7/1999 |
| WO | 9937208 | A1 | 7/1999 |
| WO | 9938449 | A1 | 8/1999 |
| WO | 9952094 | A1 | 10/1999 |
| WO | 9960939 | A1 | 12/1999 |
| WO | 0006701 | A1 | 2/2000 |
| WO | 00/10456 | A1 | 3/2000 |
| WO | 0035531 | A1 | 6/2000 |
| WO | 0130437 | A1 | 5/2001 |
| WO | 0167035 | A1 | 9/2001 |
| WO | 0187136 | A2 | 11/2001 |
| WO | 02/064011 | A2 | 8/2002 |
| WO | 02/070047 | A1 | 9/2002 |
| WO | 03086498 | A2 | 10/2003 |
| WO | 2004/023986 | A1 | 3/2004 |
| WO | 2005115235 | A1 | 12/2005 |
| WO | 2006116597 | A2 | 11/2006 |
| WO | 2008002517 | A1 | 1/2008 |
| WO | 2008042423 | A2 | 4/2008 |
| WO | 2009/150563 | A2 | 12/2009 |
| WO | 2011/104664 | A1 | 9/2011 |
| WO | 2013/158392 | A2 | 10/2013 |
| WO | 2014025550 | A1 | 2/2014 |
| WO | 2015023665 | A1 | 2/2015 |
| WO | 2016033066 | A1 | 3/2016 |

OTHER PUBLICATIONS

Extended European Search Report issued in Application No. EP 17170976.9 dated Sep. 8, 2017 (13 pages).
Australian Examination Report issued in Appl. No. AU 2017202738 dated Feb. 5, 2018 (3 pages).
Canadian Office Action issued in Appl. No. CA 2,967,198 dated May 24, 2018 (3 pages).
Australian Examination Report No. 2 issued in Appl. No. AU 2017202738 dated Jun. 25, 2018.

* cited by examiner

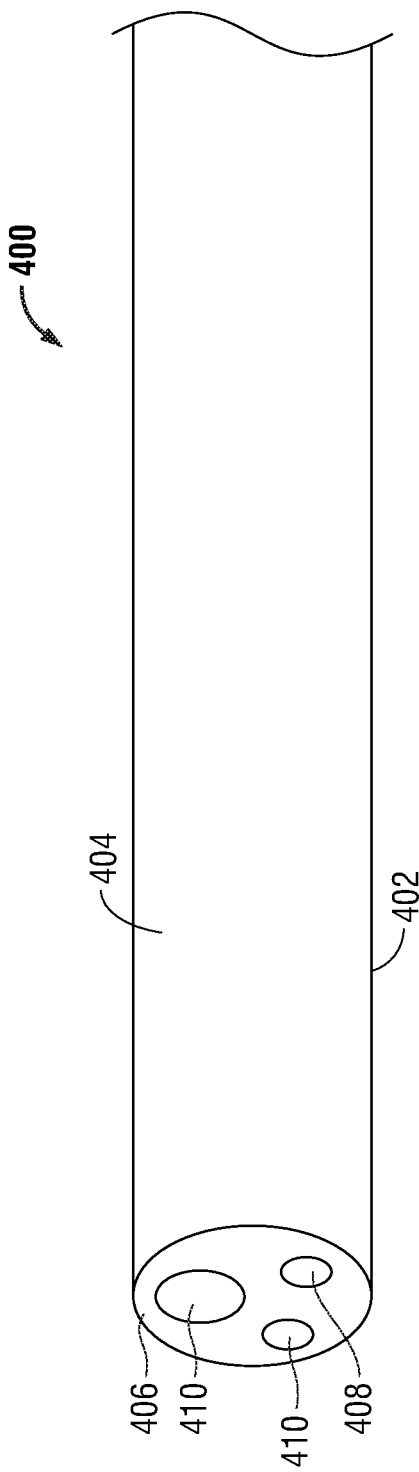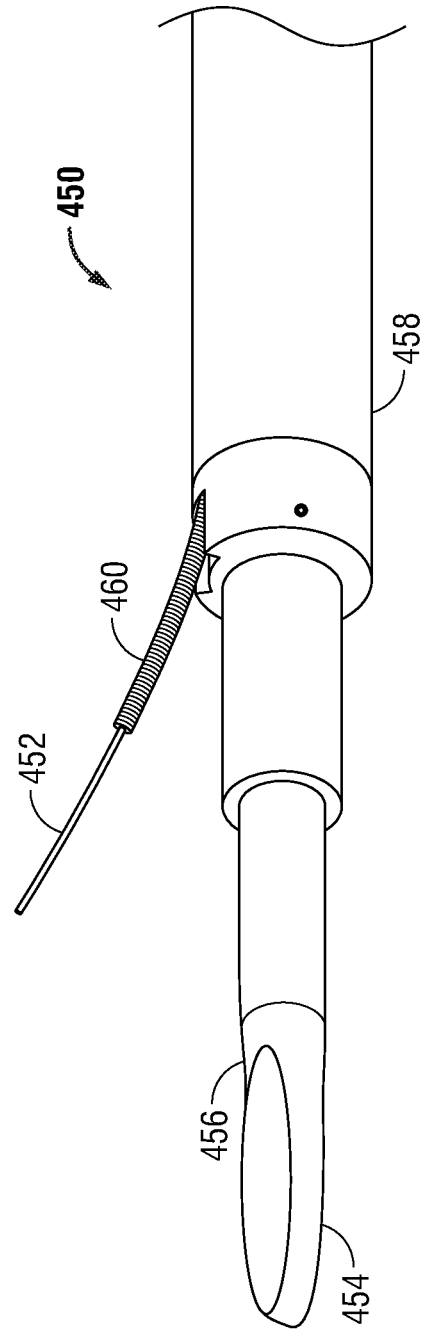
FIG. 4A
FIG. 4B

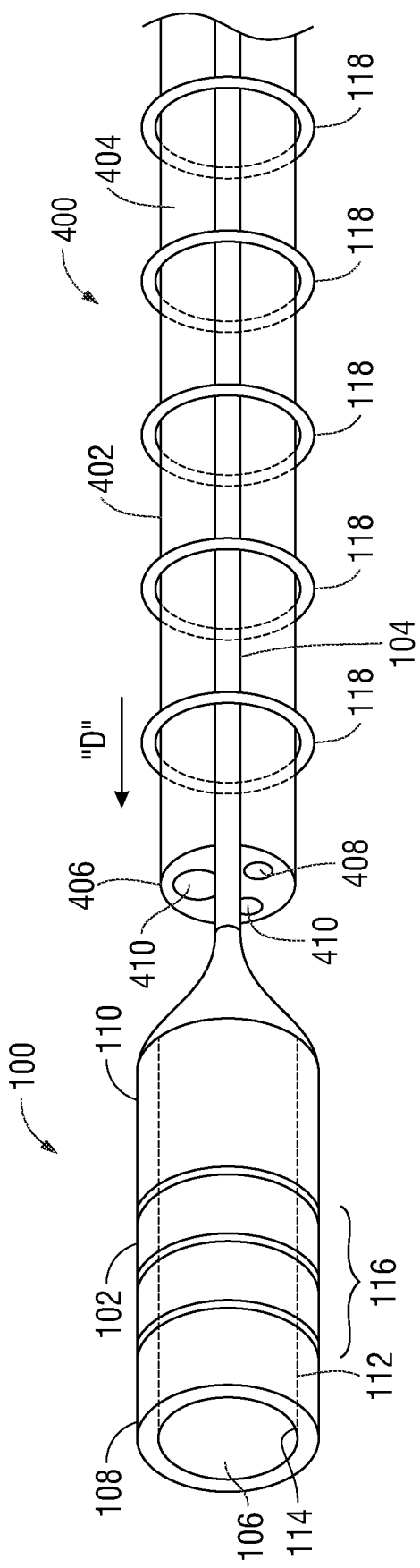
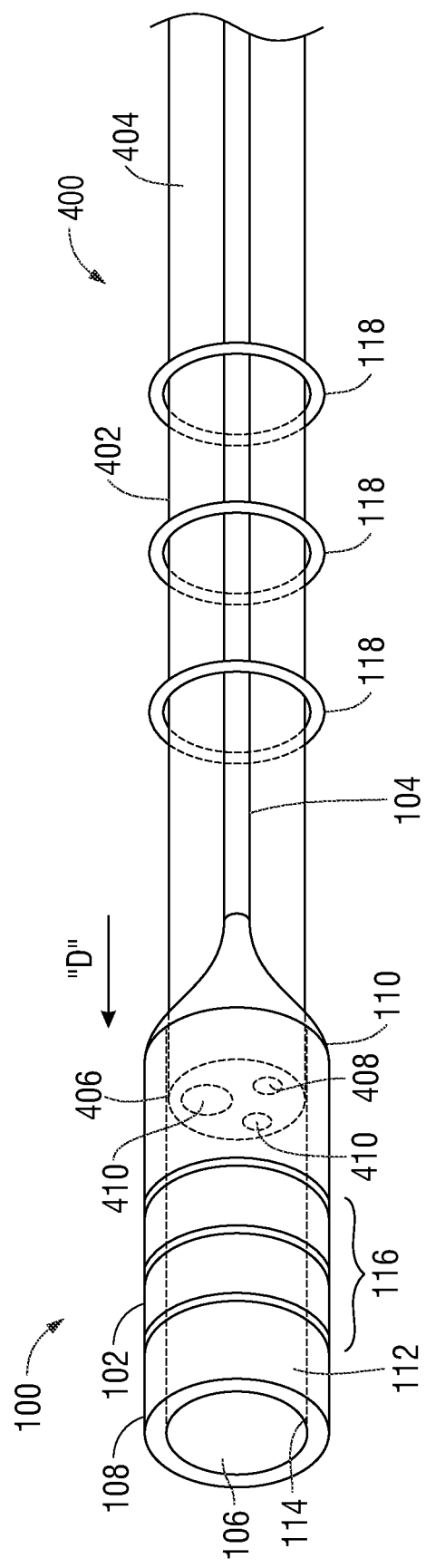
FIG. 5A
FIG. 5B

DEVICES AND SYSTEMS FOR PROVIDING SENSORS IN PARALLEL WITH MEDICAL TOOLS

CROSS REFERENCE TO RELATED APPLICATION

The present application claims the benefit of dud priority to U.S. Provisional Application Ser. No. 62/579,295 filed on Oct. 31, 2017 the entire contents of which are incorporated herein by reference.

BACKGROUND

Technical Field

The present disclosure relates to medical instruments and, more specifically, to navigation sensors applied to surgical tools.

Description of Related Art

Tools used during medical procedures include diagnostic and therapeutic scopes. Diagnostic and therapeutic scopes are devices that may be used to navigate to and inspect various areas of a patient's body. One commonly-used scope is a bronchoscope. Typically, the bronchoscope is inserted into a patient's airways through the patient's nose or mouth and can extend into the patient's lungs. A typical bronchoscope includes an elongated flexible tube having an illumination assembly for illuminating the region distal to the bronchoscope's tip, and an imaging assembly for providing a video image from the bronchoscope's tip. Various instruments, e.g., diagnostic and therapeutic instruments and/or working channels may be inserted through the bronchoscope into the patient's airways.

While navigating within a patient, it may be necessary to determine the physical location of the bronchoscope within the patient. One method for determining the physical location of the bronchoscope is through the use of sensors placed on a tool or catheter utilized with the bronchoscope. An example system that utilizes such sensors is the ILOGIC ELECTROMAGNETIC NAVIGATION BRONCHOSCOPY (ENB) system currently sold by Medtronic PLC. The details of such a system are described in commonly-assigned U.S. Pat. No. 7,233,820, filed on Mar. 29, 2004, by Gilboa and entitled "ENDOSCOPE STRUCTURES AND TECHNIQUES FOR NAVIGATING TO A TARGET IN BRANCHED STRUCTURE," the entire contents of which are incorporated herein by reference. While the system as described in U.S. Pat. No. 7,233,820 is quite capable, there is always a need for development of improvements and additions to such systems.

SUMMARY

Provided in accordance with embodiments of the present disclosure are sensor sleeves for use with tools. In an aspect of the present disclosure, a sensor sleeve includes a tubular body defining a central longitudinal axis and having a lumen defined therethrough, the tubular body being configured to receive a tool, a plurality sensors attached to the tubular body, a cabling extending distally from the tubular body, and an interface connector coupled to the cabling and configured to interface with a navigation system.

In another aspect of the present disclosure, the cabling includes a plurality of attachments configured to secure the cabling to the tool.

In a further aspect of the present disclosure, the plurality of attachments are o-rings.

In another aspect of the present disclosure, the plurality of attachments are adhesive pads.

In yet another aspect of the present disclosure, the lumen has an inner surface fabricated at least partially from a lubricious material.

In still another aspect of the present disclosure, the tubular body is fabricated at least partially from a flexible biocompatible material.

In yet another aspect of the present disclosure, the tubular body is cylindrical.

In still another aspect of the present disclosure, the plurality of sensors are selected from the group consisting of electromagnetic (EM) sensors, ultrasound sensors, optical sensors, and piezoelectric polyvinylidenefluoride (PVDF) film.

In yet another aspect of the present disclosure, the tubular body further includes a first shell and a second shell hingedly connected together along a first axis that extends in a direction parallel to the central longitudinal axis.

In a further aspect of the present disclosure, the sensor sleeve further includes a plurality of snaps attached to the first shell, and a plurality of recesses attached to the second shell.

In yet a further aspect of the present disclosure, the first shell and second shell are capable of hingedly opening along the first axis.

In another aspect of the present disclosure, the tubular body is configured to transition from a first position to a second position.

In a further aspect of the present disclosure, the first position is open and the second position is closed.

In yet a further aspect of the present disclosure, while in the first position, the first shell and the second shell are semi-cylindrical.

In another aspect of the present disclosure, while in the second position, the first shell and the second shell are connected along a second axis that extends in a direction parallel to the central longitudinal axis and the first axis.

In yet another aspect of the present disclosure, while in the second position, the plurality of snaps and the plurality of recesses are mateably engaged.

In still another aspect of the present disclosure, the tubular body is fabricated at least partially from a semi-rigid biocompatible material.

In yet another aspect of the present disclosure, the tubular body includes an opening slit along an axis that extends in a direction parallel to the central longitudinal axis.

In a further aspect of the present disclosure, the tubular body is configured to transition from an open position to a closed position along the opening slit and is self-biased in the closed position.

BRIEF DESCRIPTION OF THE DRAWINGS

Objects and features of the presently disclosed devices and systems will become apparent to those of ordinary skill in the art when descriptions of various embodiments thereof are read with reference to the accompanying drawings, wherein:

FIG. 4A is an illustration of a scope for use with the sensor sleeves of the present disclosure;

FIG. 4B is an illustration of an endobronchial ultrasound (EBUS) bronchoscopy tool for use with the sensor sleeves of the present disclosure;

FIGS. 5A-5C are sequential operational illustrations of the sensor sleeve of FIG. 1 in use with the scope of FIG. 4A at various stages, in accordance with an embodiment of the present disclosure;

DETAILED DESCRIPTION

The present disclosure is directed to devices and systems for providing sensors in parallel with surgical tools. More particularly, the present disclosure is directed to devices for retrofitting various surgical tools, such as bronchoscopes, gastroscopes, endoscopes, and ultrasound scopes (referred to hereinafter as "tools"), with navigational, visualization, and/or other sensors. In addition to the aforementioned tools, those skilled in the art will recognize that the sensors and sensor sleeves described below may also be fitted to other surgical tools, such as laparoscopic tools, thorascoscopic tools, percutaneous tools, etc. Thus, while described below as attached to scopes and other devices with lumens, those skilled in the art will recognize that the sensors and sensor sleeves may also be used with tools without lumens. The sensors may include electromagnetic (EM) sensors, optical, ultrasound, as well as other sensors providing confirmation of location and, where appropriate, further visualization and imaging capabilities for the retrofitted tools. Types of optical sensors may include confocal, near-infrared, Raman spectroscopic, optical coherence tomography, narrow band, etc. Additional examples of types of sensors usable with the present disclosure include metabolic and/or thermal sensors configured to detect positron emission tomography (PET) avid lesions, radiation sensors configured to detect to radionuclides injected into the body to detect where they cluster, as well as pH related sensors and/or protein sensors, among others.

Figure 1:
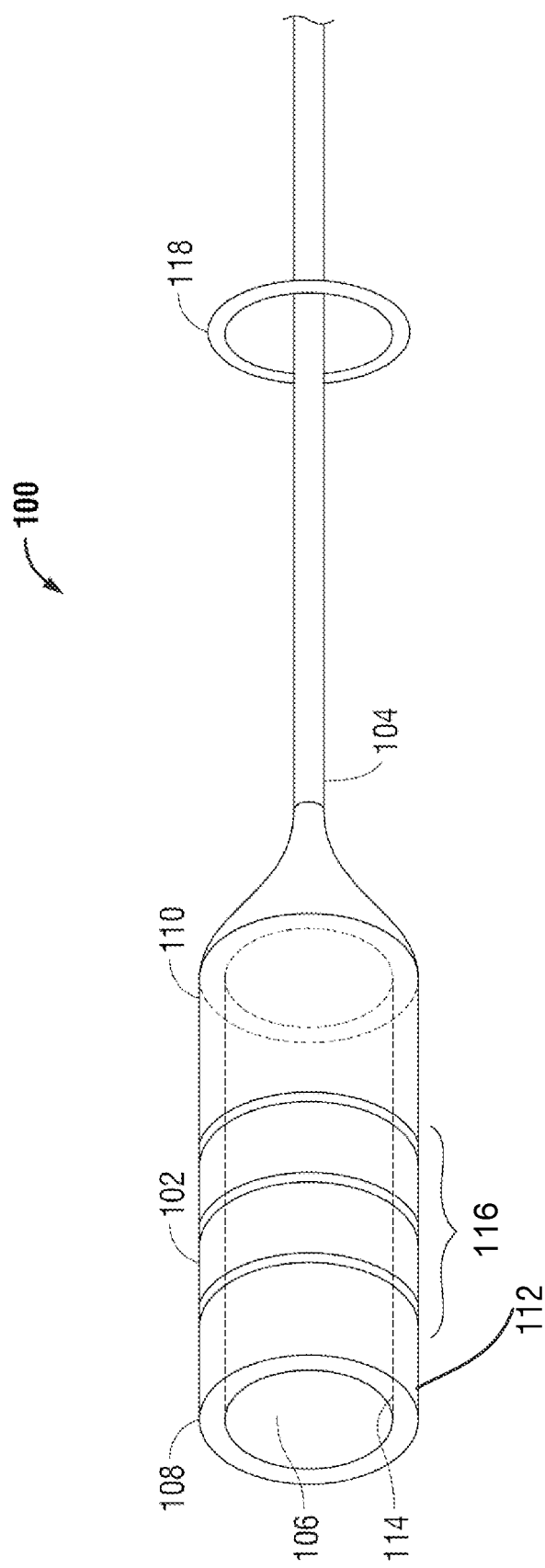
FIG. 1 is an illustration of a sensor sleeve, in accordance with one embodiment of the present disclosure.

FIG. 1 depicts a first embodiment of the present disclosure illustrating a flexible sensor sleeve 100 for enabling the tracking of the location of a tool (FIG. 4A). Sensor sleeve 100 generally includes a tubular body 102 and a cabling 104. Tubular body 102 is a hollowed tubular member having a lumen 106 extending therethrough defining a central longitudinal axis. Tubular body 102 includes a distal portion 108, proximal portion 110, outer surface 112, and inner surface 114. As illustrated in FIG. 1, included on outer surface 112 of tubular body 102 are one or more sensors 116. In other embodiments, one or more sensors 116 are located between outer surface 112 and inner surface 114 within the material forming the tubular body 102.

Figure 5C:
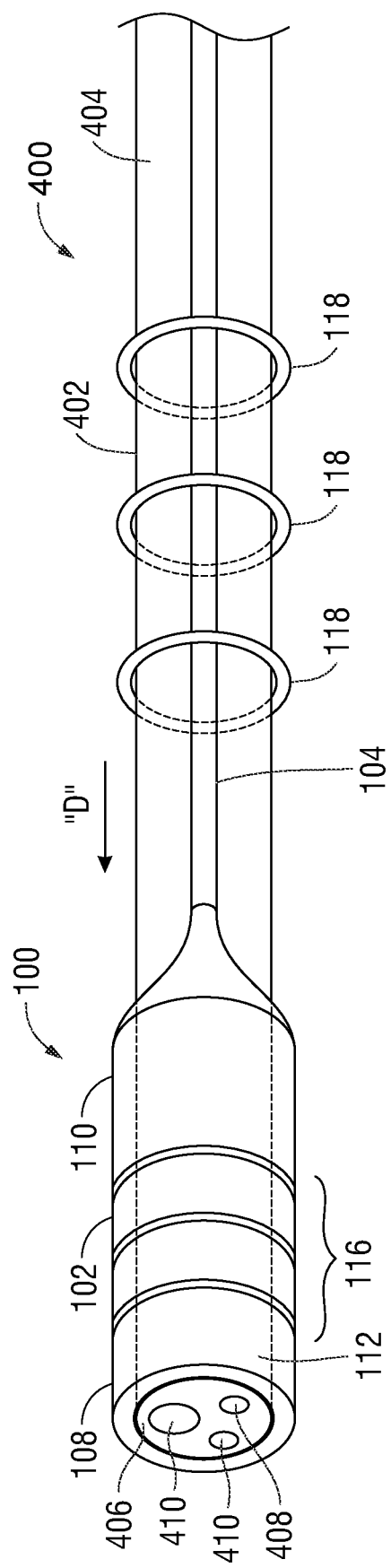
Figure 6:
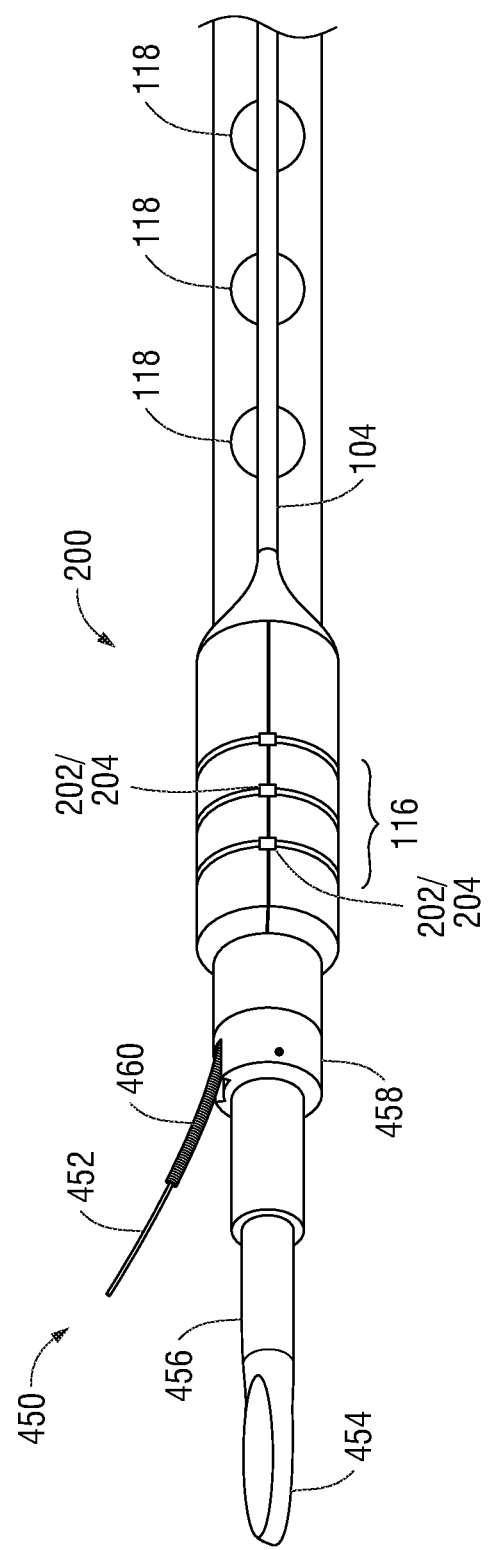
FIG. 6 is an illustration of the sensor sleeve of FIGS. 2A and 2B in use with the EBUS bronchoscopy tool of FIG. 4B, in accordance with an embodiment of the present disclosure.

Tubular body 102, as illustrated in FIG. 1, is cylindrical. It is contemplated that for sensor sleeve 100, the diameter of tubular body 102 ranges from about 2 mm to about 6 mm and is capable of being slideably fitted over similarly sized tools. In some embodiments, sensor sleeve 100 includes a cap (not shown) located at distal portion 108 which prevents further longitudinal movement of tools once fully inserted into sensor sleeve 100. Alternatively, tubular body 102 may include an area of reduced diameter proximate distal portion 108 which a tool, once fully inserted, is incapable of moving beyond. In other embodiments, as shown in FIGS. 1, 5C and 6, sensor sleeves 100 and 200 do not have a cap but remain stationary due to friction created by the interface of the tubular body 102 and the tool once inserted.

It is contemplated that sensor sleeve 100 is fabricated from flexible biocompatible materials such as silicone, urethane, thermo plastic elastomer, polyolefins, olefin copolymers, and vinyl polymers. Inner surface 114 may be formed of materials that are sufficiently lubricious that they allow a tool, such as bronchoscope 400 of FIG. 4A, to be slideably inserted. As will be appreciated by those skilled in the art, a compromise between lubricity and friction fit of tubular body 102 will result in appropriate materials being employed.

The one or more sensors 116 are, for example, EM sensors, such as those described in U.S. Pat. No. 7,233,820, optical imaging sensors, ultrasound sensors such as piezoelectric polyvinylidenefluoride (PVDF) film, and/or a combination thereof. In some embodiments, one or more sensors 116 are fabricated onto tubular body 102 of sensor sleeve 100. In further embodiments, one or more sensors 116 may be optical shape sensing fibers allowing sensing of shape and/or orientation data along an entire length of tubular body 102. Although illustrated as a plurality of rings on tubular body 102 of sensor sleeve 100, it is contemplated that one or more sensors 116 may form other configurations and shapes which provide location information. In the example of utilizing ultrasound sensors, in another embodiment, one or more sensors 116 are located at distal portion 108 of sensor sleeve 100, such that when using sensor sleeve 100, ultrasound imaging may be undertaken. One or more sensors 116 may be configured to connect to a workstation, such as workstation 780 (FIG. 7), via wired and/or wireless connection. For example, one or more sensors 116 may be connected to workstation 780 via one or more wires included in cabling 104 and/or via a wireless connection, such as a BLUETOOTH connection. In embodiments, the one or more sensors 116 may include a printed circuit board with wired and/or wireless communication capability for communicating image data and/or other interrogation or sensed data. The one or more sensors 116 may further include batteries and/or other wireless power capability.

In the embodiment using EM sensors, once attached to a tool, one or more sensors 116 creates a six degrees-of-freedom EM tracking system (similar to those disclosed in U.S. Pat. No. 6,188,355 and published PCT Application Nos. WO 00/10456 and WO 01/67035, the entire contents of each of which are incorporated herein by reference, or any other suitable position measuring system), to be utilized for performing navigation and as further described in the detailed description of FIG. 7.

Figure 2A:
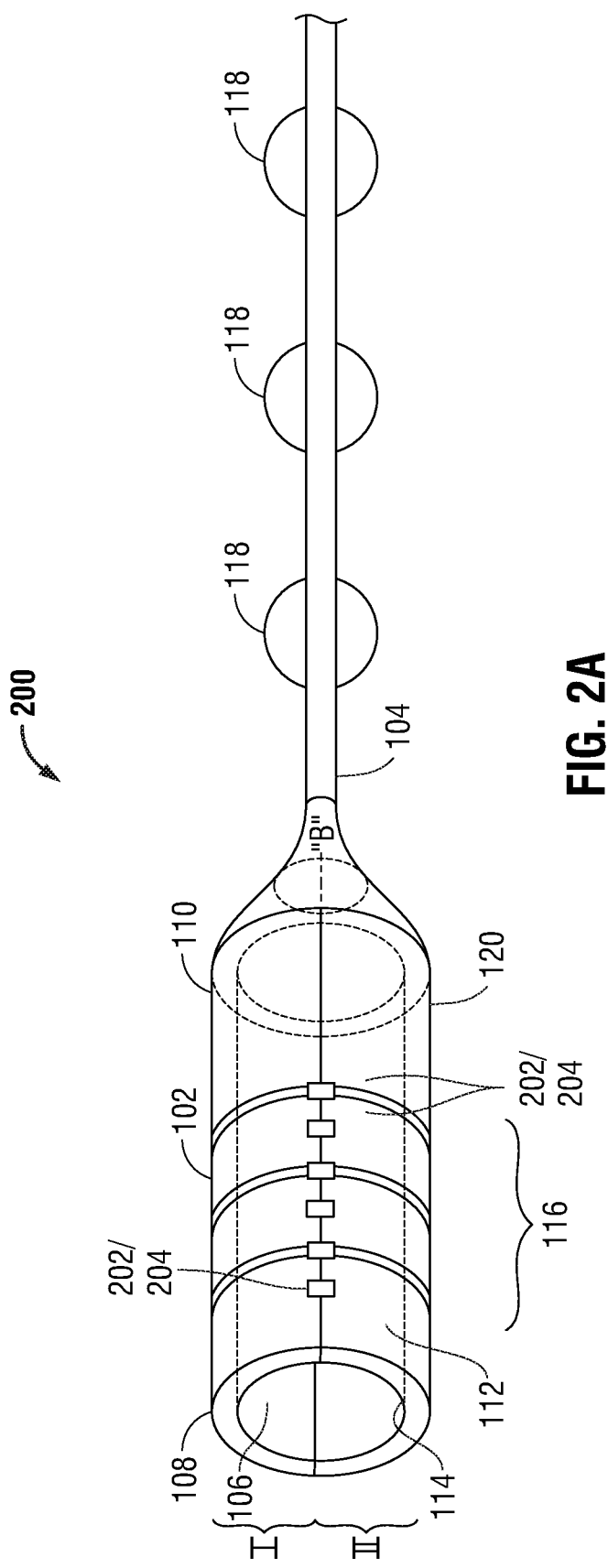
FIG. 2A is an illustration of a sensor sleeve in a closed position, in accordance with a second embodiment of the present disclosure.
Figure 2B:
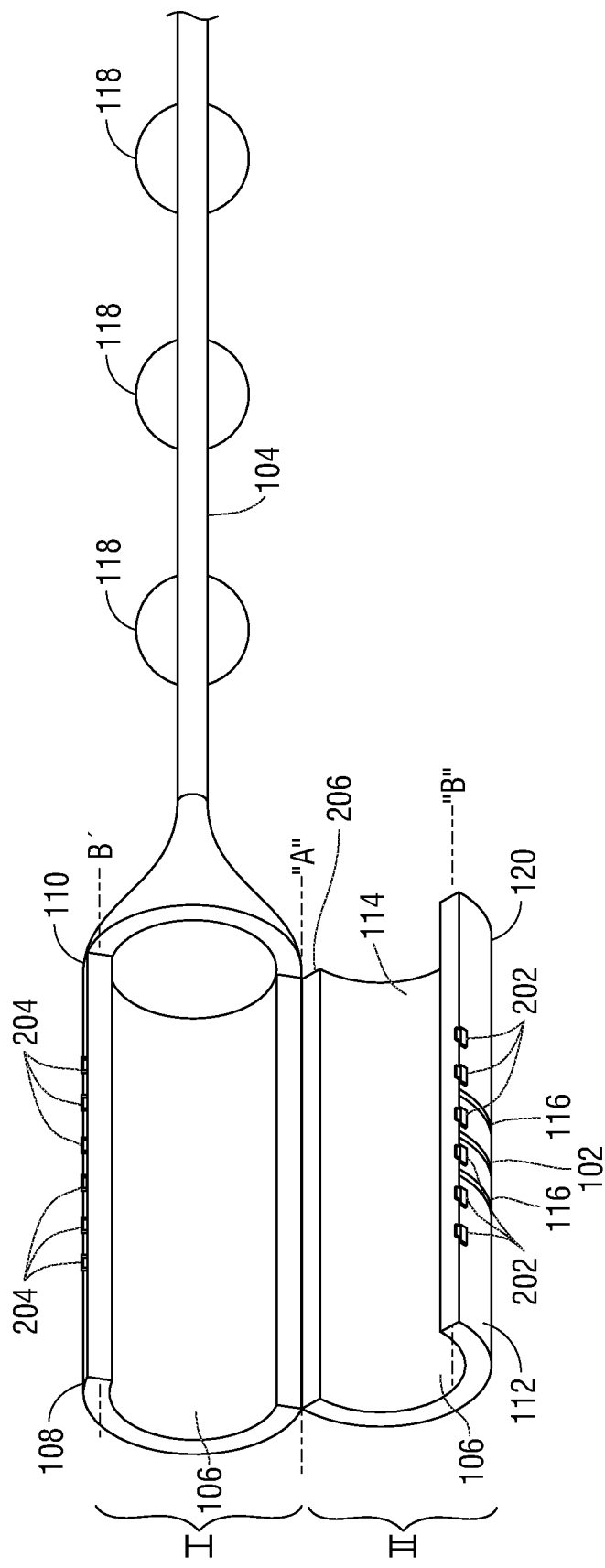
FIG. 2B is an illustration of the sensor sleeve of FIG. 2A in an open position, in accordance with the second embodiment of the present disclosure.
Figure 3:
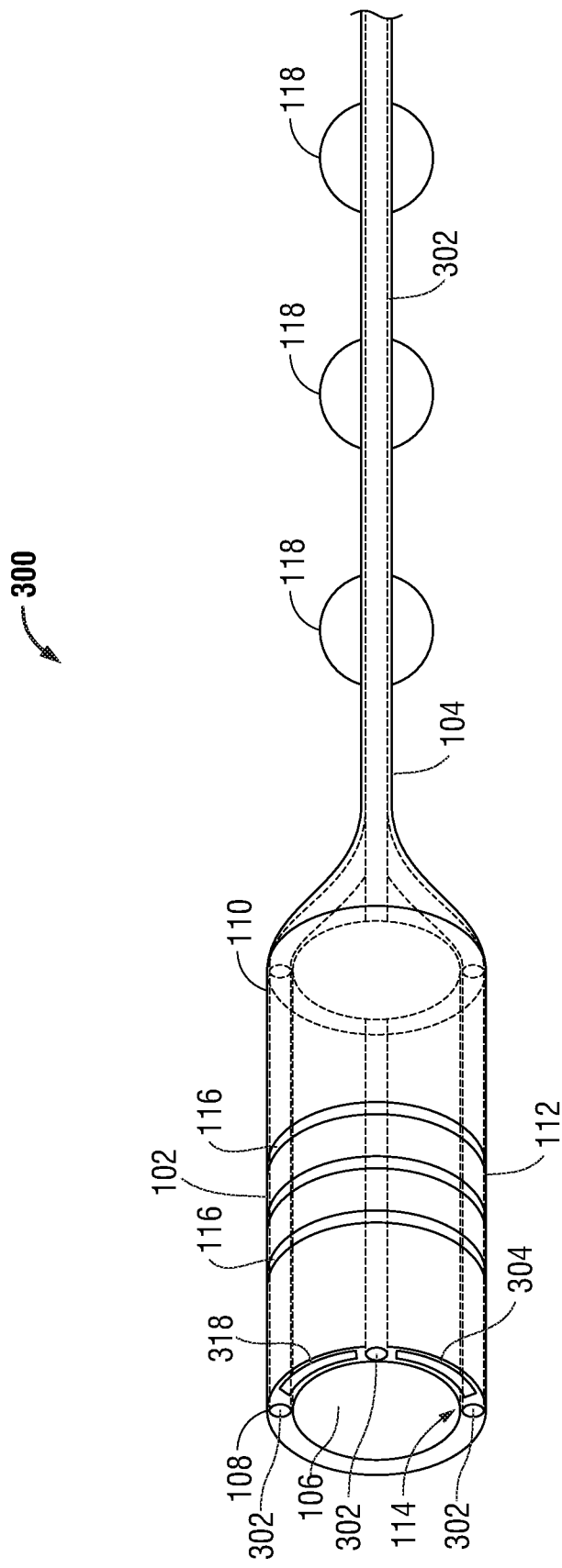
FIG. 3 is an illustration of a sensor sleeve including optical sensors, in accordance with an embodiment of the present disclosure.
Figure 7:
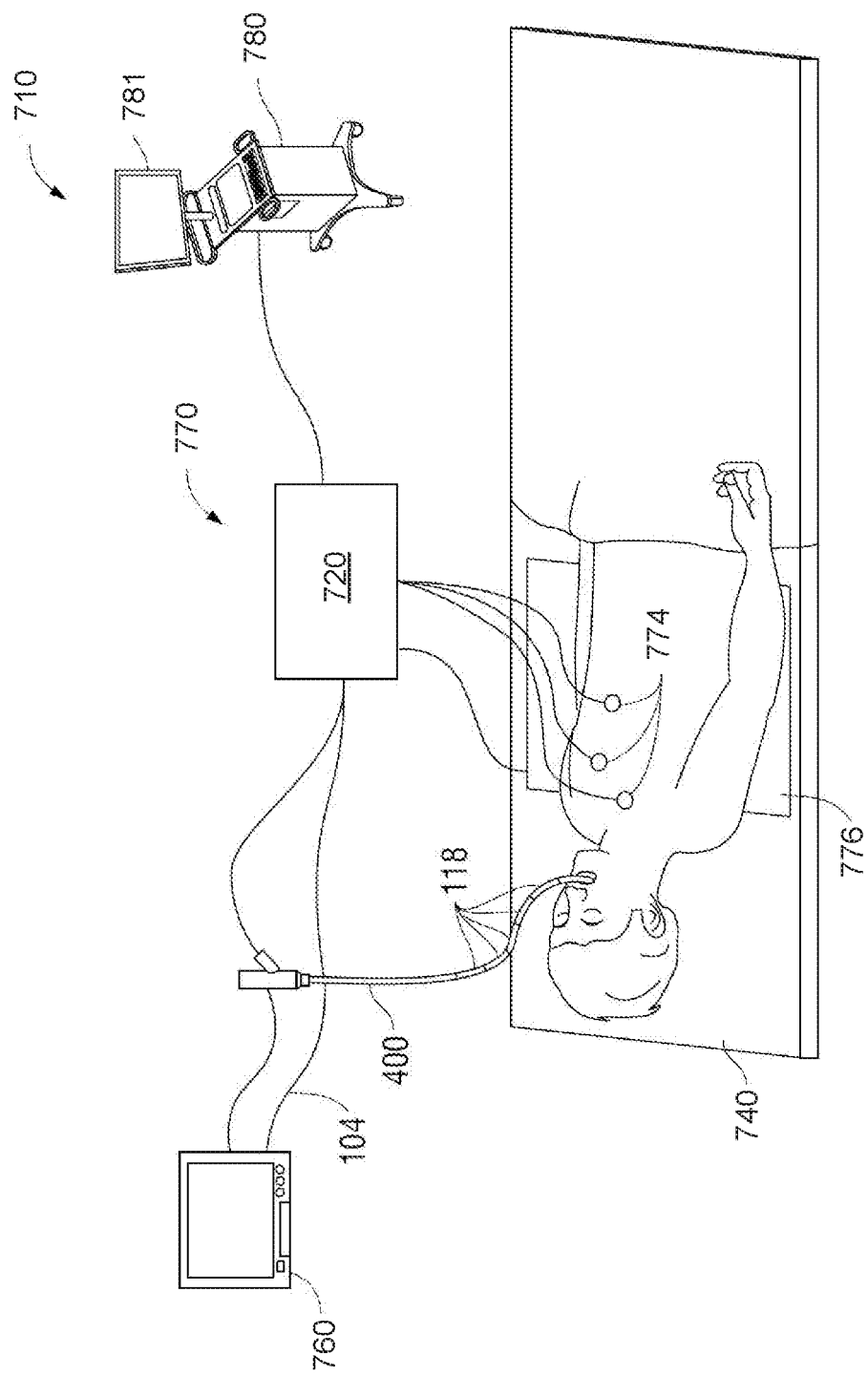
FIG. 7 illustrates an endobronchial navigation system which may be utilized with the present disclosure.

Cabling 104 is illustrated as coupled to proximal portion 110 of tubular body 102 and includes one or more attachments 118. In one embodiment, and as shown in FIG. 1, one or more attachments 118 are o-rings, which are configured to slideably receive a body of a tool and frictionally attach the body of the tool to cabling 104. In a further embodiment, and as shown in FIGS. 2A, 2B, and 3, one or more attachments 118 are adhesive tabs which are configured to adhesively attach cabling 104 to a body of the tool. It is further contemplated that cabling 104 includes, at a proximal end, one or more interface connectors (not shown) configured to be interfaced with a navigation system or an imaging system, such as a ultrasound imaging system, as shown in FIG. 7. One or more interface connectors may be the in form of a universal serial bus (USB) 3.0, two or three-prong power plug, and/or banana plugs.

Referring now to FIGS. 2A and 2B, an illustration of a second embodiment of a rigid or semi-rigid sensor sleeve 200 is shown. As further detailed in the description of FIG. 2B, sensor sleeve 200 is capable of being opened from a first closed position (FIG. 2A) to a second open position (FIG. 2B). As illustrated in FIG. 2A, similar to sensor sleeve 100 of FIG. 1, sensor sleeve 200 has a tubular body 102 and cabling 104. Tubular body 102 includes a lumen 106 extending therethrough defining a longitudinal axis, distal portion 108, proximal portion 110, outer surface 112, and inner surface 114. Included on outer surface 112 of tubular body 102 are one or more sensors 116. In other embodiments, one or more sensors 116 are located between outer surface 112 and inner surface 114, depending on the type of sensor utilized. Further, included in sensor sleeve 200, on outer surface 112 of tubular body 102, are one or more snaps 202 and one or more recesses 204, as illustrated in the closed position in FIG. 2A. Once in a closed position, a connection is formed along axis "B" between one or more snaps 202 and one or more recesses 204. As further shown in FIG. 2A, axis "B" divides a first portion "I" and a second portion "II" of sensor sleeve 200 as sensor sleeve 200 is transitioned to an open position.

Similar to FIG. 1, tubular body 102, as illustrated in FIG. 2A, is cylindrical. It is contemplated that for sensor sleeve 200, the diameter of tubular body 102 ranges from 2 mm to 6 mm and is capable of being snap-fitted over similarly sized small tools, and is fabricated from both rigid or semi-rigid and flexible lubricious biocompatible materials such as silicone.

Referring now to FIG. 2B, sensor sleeve 200 is illustrated in an open position. As shown in FIG. 2B, sensor sleeve 200 is capable of being hingedly opened about longitudinally axis "A." Once in the opened position, sensor sleeve 200 is separated into first portion "I" and second portion "II" and each is connected by hinge 206 along axis "A." As shown in FIG. 2B, cabling 104 is attached to first portion "I." It is contemplated that cabling 104 may be attached to either first portion "I" or second portion "II."

One or more snaps 202 are illustrated as a plurality of tabs and one of more recesses 204 are illustrated as recesses which are configured to receive the one or more snaps 202. Each of one or more recesses 204 and one or more snaps 202 is shown along edges B and B' of the tubular body 102. Once closed, edges "B" and "B'" have the recesses 204 and snaps 202 mate to secure the tubular body 102 around a tool. Although sensor sleeve 200 is illustrated as a rigid or semi-rigid sleeve in a hingedly opened position with one of more recesses 204 and one or more snaps 202 used together to secure sensor sleeve 200 in a closed position, in other embodiments a sensor sleeve similar to sensor sleeve 200 does not include one or more recesses 204 and one or more snaps 202 and is fabricated from a flexible material which is self-biased, based on the fabricated material, in a closed position, with an opening slit defining edges "B" and "B'". In this embodiment, a user may open the sensor sleeve, insert a tool, such as those shown in FIGS. 4A and 4B, and allow the elasticity of the material of the sensor sleeve 200 to close around and secure the tubular body 102 to the tool.

FIG. 3 depicts a sensor sleeve 300 similar to sensor sleeve 100, but including optical imaging sensors. Included within tubular body 102 are one or more fiber optic cables 302 and one or more optical sensors 304. As illustrated in FIG. 3, one of more fiber optic cables 302 are located inside of tubular body 102 between outer surface 112 and inner surface 114.

Fiber optic cables 302 are illustrated as fabricated within tubular body 102 and extend throughout tubular body 102 from proximal portion 110 to distal portion 108. Fiber optic cables 302 are utilized to emit light from distal portion 108 of sensor sleeve 300, which may be reflected and received by one or more optical sensors 304. Fiber optic cables extend through tubular body 102 from distal portion 108 through cabling 104. Alternatively, they may be formed on outer surface 112. It is contemplated that optical sensors 304 may be used either alone or in combination with one or more sensors 116. Such a configuration may be particularly useful with an endobronchial ultrasound (EBUS) scope or a radial endobronchial ultrasound (REBUS) scope enabling not only ultrasound imaging but also EM navigation, as described above, and optical imaging. As shown in FIG. 3, multiple fiber optic cables are depicted, however only one is necessary and the use of multiple optical sensors may enable greater clarity of and a wider field of view. This may be accomplished by forming composite images based on the combined optical data received by one or more optical sensors 304.

FIGS. 4A and 4B, depict two examples of tools 400, 450, which may employ the sensor sleeves 100, 200, and/or 300. FIG. 4A illustrates the distal portion of a tool 400 utilized to view images inside of a patient's airways. Tool 400 includes a body portion 402, which is inserted into a patient's airways. Body portion 402 includes surface 404 and a distal face 406, which includes an imaging lens 408 configured to permit optical viewing of the patient's airways, and a plurality of working channels 410. As described herein, sensor sleeves 100, 200, and/or 300 are configured to receive tool 400 or another tool similar in size to tool 400.

FIG. 4B illustrates an EBUS 450 with transbronchial needle 452 for use during an ultrasound procedure. EBUS 450 includes an ultrasound imager 454 at a distal portion 456 of body 458. Generally, ultrasound imager 454 allows a clinician to image endobronchial structures with ultrasound. Optionally, EBUS 450 may, in some instances, include a retractable channel 460 through which retractable transbronchial needle 452 may be inserted. Based on the depicted configuration, it is possible to obtain tissue samples while under ultrasound visualization. Generally, retractable channel 460 is a hollowed tube through which retractable transbronchial needle 452 can be advanced. In the illustration of FIG. 4B, retractable channel 460 and retractable transbronchial needle 452 are each shown in a fully extended position. In the fully retracted position, both retractable channel 460 and retractable transbronchial needle 452 are located within the interior of EBUS 450.

Referring now to FIGS. 5A-5C, illustrations of tool 400 as it is received by sensor sleeve 100 in three stages are shown. FIG. 5A illustrates tool 400 prior to insertion into sensor sleeve 100 in direction "D." As shown in FIG. 5A, tool 400 is located completely outside of lumen 106 of sensor sleeve 100 with distal face 406 of tool 400 in alignment with proximal portion 110 of sensor sleeve. In the embodiment shown in FIGS. 5A-5C, one or more attachments 118 are o-rings, and tool 400 is inserted through each of one or more attachments 118 prior to tool 400 being inserted into sensor sleeve 100. In another embodiment where one or more attachments 118 are adhesive tabs, during this stage of insertion of tool 400, one or more attachments 118 are not adhered to surface 404 of tool 400.

FIG. 5B illustrates tool 400 as it is partially inserted into sensor sleeve 100 in direction "D." As shown in FIG. 5B, sensor sleeve 100 has received distal face 406 of tool 400. Once received, it is contemplated that inner surface 114 of sensor sleeve 100 will be in physical contact with surface 404 of tool 400. Because inner surface 114 is generally fabricated from material that is sufficiently lubricious, tool 400 is capable of being slideably received by sensor sleeve 100, while also remaining frictionally engaged. Further, sensor sleeve 100 may be formed of an elastic material allowing it to expand slightly to receive tool 400 and secure the sensor sleeve 100 to tool 400.

Referring now to FIG. 5C, tool 400 is illustrated as being fully received by sensor sleeve 100. Once tool 400 is fully inserted into sensor sleeve 100, distal portion 108 of sensor sleeve 100 is parallel with distal face 406 of tool 400. As shown in FIG. 5C, tool 400 is shown as inserted through each of one or more attachments 118, which are shown as o-rings around body 402 of tool 400. In other embodiments, one or more attachments 118 are adhesive attachments which are attached to surface 404 of tool 400. It is contemplated that once fully inserted into sensor sleeve 100, tool 400 is frictionally engaged with sensor sleeve 100 such that, following insertion of tool 400 into the airways of a patient and movement therein, sensor sleeve 100 remains engaged with tool 400.

FIG. 6, similar to FIG. 5C, depicts EBUS 450 with transbronchial needle 452 as being fully received by sensor sleeve 200. As shown in FIG. 6, retractable transbronchial needle 452 is extended laterally from body 458 of EBUS 450. As described in the description of FIGS. 2A and 2B, prior to insertion of EBUS 400 into sensor sleeve 200, sensor sleeve 200 may be opened by parting one of more snaps 202 from one of more recesses 204 and inserting EBUS 420 into sensor sleeve 200. Once EBUS 400 is inserted, sensor sleeve 200 may be closed around EBUS 450 by connecting one or more snaps 202 with one of more recesses 204. After sensor sleeve 200 is closed around EBUS 450, sensor sleeve 200 may be slideably moved towards retractable channel 460. Once slideably moved towards retractable channel 460, one or more attachments 118 may be adhesively attached to the surface of body 458 of EBUS 400. In other embodiments, one or more attachments 118 are o-rings which are slideably engaged around body 458 of EBUS 400. It is contemplated that once fully inserted into sensor sleeve 200, EBUS 450 is frictionally engaged with sensor sleeve 200 such that during movement within and insertion of EBUS 450 into the airways of a patient, sensor sleeve 200 remains engaged with EBUS 450. Although illustrated using sensor sleeve 200, as described in the description of FIG. 4, retractable channel 460 and retractable transbronchial needle 452 may be retracted into EBUS 400 and once retracted into EBUS 400, EBUS 400 may be received by a sensor sleeve similar to sensor sleeve 100, 300 and those described herein.

With reference now to FIG. 7, an EM navigation (EMN) system 710 to be utilized in conjunction with the present disclosure is shown. EMN system 710 generally includes an operating table 740 configured to support a patient; a bronchoscope 750 (such as tool 400) configured for insertion through the patient's mouth and/or nose into the patient's airways; monitoring equipment 760 coupled to bronchoscope 750 for displaying video images received from bronchoscope 750; a tracking system 770 including a tracking module 772, a plurality of reference sensors 774, an EM field generator 776; and a workstation 780 including software and/or hardware used to facilitate pathway planning, identification of the region of interest, and navigation to the region of interest.

As illustrated in FIG. 7, the patient is shown lying on operating table 740 with tool 400 with sensor sleeve 100 attached and inserted through the patient's mouth and into the patient's airways. Tool 400 includes a source of illumination and a video imaging system (not explicitly shown) and is coupled to monitoring equipment 760, e.g., a video display, for displaying the video images received from the video imaging system of tool 400. As shown in FIG. 7, sensor sleeve is attached to tool 400 with one or more attachments 118, illustrated as o-rings slideably receiving tool 400. Cabling 104 is illustrated as interfaced with monitoring equipment 760 and tracking module 772.

As further shown in FIG. 7, EM field generator 776 is positioned beneath the patient. EM field generator 776 and the plurality of reference sensors 774 are interconnected with tracking module 772, which derives the location of each reference sensor 774 in six degrees of freedom. Tracking module 772 is configured to track the position of one or more sensors 116 as it moves in conjunction with tool 400 while within a patient. In accordance with one aspect of the present disclosure, an EM field is generated by an EM field generator 776. The location of one or more sensors 116 and therefore the location the tool 400 can be determined based on currents induced in the one or more sensors 116 by the EM field. The induced current is fed to workstation 180 which includes application 781 and can convert the detected current to a location mapped to the field generated by the EM field generator. An example of such a tracking system employing an EM field is the SUPERDIMENSION navigation system currently offered by Medtronic PLC. Similarly, one or more of reference sensors 774, once attached to the chest of the patient, allow the six degrees of freedom coordinates to be sent to workstation 180, which includes application 781 where data from one or more reference sensors 774 is used to calculate a patient coordinate frame of reference.

In another embodiment, the position of one or more sensors 116 relative to diseased tissue may be determined based on impedance characteristics of tissue surrounding the one or more sensors 116. Diseased tissue, in any part of the body, will have different characteristics than the surrounding tissue, and thus the distance from which diseased tissue can be identified will vary. For example, depending on the type of disease, diseased tissue may be identified up to 2 centimeters, or even up to 4 centimeters, from sensors 116. Thus, a diseased area of, for example, the lung may have different impedance characteristics than the surrounding normal tissue such that a sound signal will return at a different frequency from what was transmitted (even without converting it into a picture). This would similarly apply to the spectrum of returning optical wavelengths (visible, infrared, or ultraviolet). The same concepts apply to metabolic, radiation, and other types of sensors. By using such frequency-based interrogation methods, placement of the one or more sensors 116 (and thus tool 400) relative to healthy and diseased tissue at a diagnostic or treatment location may be determined based on the impedance characteristics of the surrounding tissue.

Based on the foregoing disclosures, tools are capable of being retrofitted with a sensor sleeve, which provides independent sensors to be utilized with the tool. Embodiments of the presently disclosed surgical systems and devices are described in detail with reference to the drawings wherein like references numerals identify similar or identical elements. In the drawings, and in the foregoing description, the term "proximal" should be understood as referring to the portion or end of the apparatus, or component thereof, that is closest to a user during proper use, while the term "distal" should be understood as referring to the portion or end of the apparatus, or component thereof, that is furthest from a user during proper use, as is traditional and conventional in the art. These detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in virtually any appropriately detailed structure.

What is claimed is:

1. A sensor sleeve for use with a tool, the sensor sleeve comprising:
    a tubular body having a proximal end and a distal end, defining a central longitudinal axis, and having a lumen defined therethrough, the tubular body being configured to receive the tool through the lumen;
    a plurality of sensors attached to the tubular body;
    a cabling extending proximally from the proximal end of the tubular body, the cabling comprising an outer surface and a plurality of o-rings,
    wherein the o-rings are configured to be coupled to the outer surface of the cabling and to secure the cabling to an outside surface of the tool, wherein the outside surface of the tool and the outside surface of the cabling are against an inner surface of the plurality of o-rings when the tool is disposed through the plurality of o-rings; and
    an interface connector coupled to the cabling and configured to interface with a navigation system.

2. The sensor sleeve according to claim 1, wherein the lumen has an inner surface fabricated at least partially from a lubricious material.

3. The sensor sleeve according to claim 1, wherein the tubular body is fabricated at least partially from a flexible biocompatible material.

4. The sensor sleeve according to claim 1, wherein the tubular body is cylindrical.

5. The sensor sleeve according to claim 1, wherein the plurality of sensors is selected from the group consisting of electromagnetic (EM) sensors, ultrasound sensors, optical sensors, and piezoelectric polyvinylidenefluoride (PVDF) film.

6. The sensor sleeve according to claim 1, wherein the tubular body further includes a first shell and a second shell hingedly connected together along a first axis that extends in a direction parallel to the central longitudinal axis.

7. The sensor sleeve according to claim 6, further including:
    a plurality of snaps attached to the first shell; and
    a plurality of recesses attached to the second shell.

8. The sensor sleeve according to claim 7, wherein the first shell and second shell are capable of hingedly opening along the first axis.

9. The sensor sleeve according to claim 7, wherein the tubular body is configured to transition from a first position to a second position.

10. The sensor sleeve according to claim 9, wherein the first position is open and the second position is closed.

11. The sensor sleeve according to claim 10, wherein, while in the first position, the first shell and the second shell are semi-cylindrical.

12. The sensor sleeve according to claim 10, wherein, while in the second position, the first shell and the second shell are connected along a second axis that extends in a direction parallel to the central longitudinal axis and the first axis.

13. The sensor sleeve according to claim 10, wherein, while in the second position, the plurality of snaps and the plurality of recesses are mateably engaged.

14. The sensor sleeve according to claim 6, wherein the tubular body is fabricated at least partially from a semi-rigid biocompatible material.

15. The sensor sleeve according to claim 1, wherein the tubular body includes an opening slit along an axis that extends in a direction parallel to the central longitudinal axis.

16. The sensor sleeve according to claim 15, wherein the tubular body is configured to transition from an open position to a closed position along the opening slit and is self-biased in the closed position.

* * * * *